United States Patent
Sakurai et al.

(10) Patent No.: US 12,104,245 B2
(45) Date of Patent: Oct. 1, 2024

(54) COMPOUND, THIN-FILM FORMING RAW MATERIAL THAT CONTAINS SAID COMPOUND, AND METHOD OF MANUFACTURING THIN FILM

(71) Applicant: ADEKA CORPORATION, Tokyo (JP)

(72) Inventors: Atsushi Sakurai, Tokyo (JP); Masako Hatase, Tokyo (JP); Masaki Enzu, Tokyo (JP); Keisuke Takeda, Tokyo (JP); Ryota Fukushima, Tokyo (JP); Atsushi Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 173 days.

(21) Appl. No.: 17/771,181

(22) PCT Filed: Oct. 19, 2020

(86) PCT No.: PCT/JP2020/039239
§ 371 (c)(1),
(2) Date: Apr. 22, 2022

(87) PCT Pub. No.: WO2021/085210
PCT Pub. Date: May 6, 2021

(65) Prior Publication Data
US 2022/0389570 A1    Dec. 8, 2022

(30) Foreign Application Priority Data

Nov. 1, 2019   (JP) ................. 2019-199862

(51) Int. Cl.
| | | |
|---|---|---|
| C23C 16/18 | (2006.01) | |
| C07D 487/10 | (2006.01) | |
| C07F 1/00 | (2006.01) | |
| C07F 3/00 | (2006.01) | |
| C07F 7/22 | (2006.01) | |
| C07F 13/00 | (2006.01) | |
| C07F 15/04 | (2006.01) | |
| C07F 15/06 | (2006.01) | |
| C23C 16/455 | (2006.01) | |

(52) U.S. Cl.
CPC ............ *C23C 16/18* (2013.01); *C07D 487/10* (2013.01); *C07F 1/005* (2013.01); *C07F 3/003* (2013.01); *C07F 7/2284* (2013.01); *C07F 13/005* (2013.01); *C07F 15/045* (2013.01); *C07F 15/065* (2013.01); *C23C 16/45553* (2013.01)

(58) Field of Classification Search
None
See application file for complete search history.

(56) References Cited

U.S. PATENT DOCUMENTS

| | | |
|---|---|---|
| 2012/0308739 A1 | 12/2012 | Lansalot-Matras et al. |
| 2023/0142848 A1* | 5/2023 | Fukushima ....... C23C 16/45553 427/255.33 |

FOREIGN PATENT DOCUMENTS

| | | |
|---|---|---|
| CN | 101274939 | 10/2008 |
| JP | 2009-503247 | 1/2009 |
| JP | 5003978 | 8/2012 |
| JP | 5181292 | 4/2013 |
| RU | 2 146 260 | 3/2000 |
| RU | 2146260 C1 * | 3/2000 |
| WO | 2007/002672 | 1/2007 |
| WO | 2007/002673 | 1/2007 |
| WO | 2007/002674 | 1/2007 |

OTHER PUBLICATIONS

CAS Abstract and Indexed Compounds for O. Petrova et al., RU 2146260 C1 (2000) (Year: 2000).*
B. Korybut-Daszkiewicz et al., 23 Inorganic Chemistry, 903-914 (1984) (Year: 1984).*
CAS Abstract and Indexed Compound, B. Korybut-Daszkiewicz et al., 23 Inorganic Chemistry, 903-914 (1984) (Year: 1984).*
B. Nishat et al., 34 Synthesis and Reactivity in Inorganic and Metal-Organic Chemistry, 335-351 (2004) (Year: 2004).*
CAS Abstract and Indexed Compounds, B. Nishat et al., 34 Synthesis and Reactivity in Inorganic and Metal-Organic Chemistry, 335-351 (2004) (Year: 2004).*
A. Phillips et al., 30 Organometallics 6119-6132 (2011) (Year: 2011).*
International Search Report issued Dec. 8, 2020 in International (PCT) Application No. PCT/JP2020/039239.
Jespersen et al., "Supercritical fluids applied to the sol-gel process for preparation of AEROMOSILS/palladium particle nanocomposite catalyst", Journal of Supercritical Fluids, 2008, vol. 46, No. 2, pp. 178-184.
Kucherov et al., "Comparative Study of Cu(II) Catalytic Sites Immobilized onto Different Polymeric Supports", Macromolecular Symposia, 2003, vol. 204, pp. 175-189.

(Continued)

*Primary Examiner* — Alexander R Pagano
(74) *Attorney, Agent, or Firm* — Wenderoth, Lind & Ponack, L.L.P.

(57) ABSTRACT

Provided is a thin-film forming raw material containing a compound represented by the following formula (1):

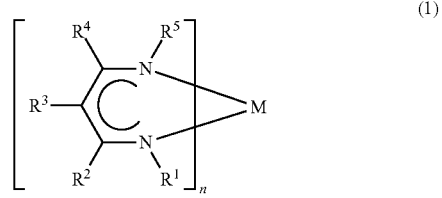

(1)

in the formula (1), $R^1$ to $R^5$ each independently represent a hydrogen atom, an alkyl group having 1 to 5 carbon atoms, or a group containing a fluorine atom, M represents a metal atom, and "n" represents a valence of the metal atom represented by M, provided that at least one of $R^2$, $R^3$, and $R^4$ represents the group containing a fluorine atom.

5 Claims, 5 Drawing Sheets

(56) References Cited

OTHER PUBLICATIONS

Bozbag et al., "Thermodynamic Control of Metal Loading and Composition of Carbon Aerogel Supported Pt—Cu Alloy Nanoparticles by Supercritical Deposition", Journal of Physical Chemistry C, 2013, vol. 117, No. 13, pp. 6777-6787.

Bukalov et al., "Non-rigid molecule of copper (II) diiminate Cu[$CF_3$C(NH)C(F)C(NH)$CF_3$]2, its conformational polymorphism in crystal and structure in solutions (Raman, UV-vis and quantum chemistry study)", Journal of Molecular Structure, 2015, vol. 1098, pp. 246-254.

Shreider, "Electrochemical synthesis and properties of some metal Perfluoro-β-diketdiiminates", Inorganica Chimica Acta, 1982, vol. 64, No. 3, pp. L101-L103.

* cited by examiner

COMPOUND, THIN-FILM FORMING RAW MATERIAL THAT CONTAINS SAID COMPOUND, AND METHOD OF MANUFACTURING THIN FILM

TECHNICAL FIELD

The present invention relates to a novel compound, a thin-film forming raw material including the compound, a method of using the compound as a precursor, a thin-film manufactured by using the method, and a method of manufacturing a thin-film.

BACKGROUND ART

In the field of electronic devices, such as a semiconductor, a photovoltaic cell, and a display material, a compound having a β-diketiminate ligand is known as a raw material for a thin-film having conductivity. As a method of manufacturing the thin-film, there are given, for example, a sputtering method, an ion plating method, metal organic decomposition (MOD) methods, such as a coating thermal decomposition method and a sol-gel method, and chemical vapor deposition (CVD) methods. Of those, an atomic layer deposition (ALD) method, which is one kind of the CVD methods, is the optimum production process for the thin-film because the method has many advantages, such as excellent composition controllability and step coverage, suitability for mass production, and capability of hybrid integration.

For example, in each of Patent Documents 1 to 3, there is proposed a method of forming a metal-containing thin-film through use of a compound having a β-diketiminate ligand by the ALD method.

CITATION LIST

Patent Document

Patent Document 1: JP 5181292 B2
Patent Document 2: JP 5003978 B2
Patent Document 3: JP 2009-503247 A

SUMMARY OF INVENTION

Technical Problem

When a metal-containing thin-film is formed on the surface of a substrate by the CVD method, a thin-film forming raw material that has a high vapor pressure, has a low melting point, and is capable of forming a high-quality metal-containing thin-film is required. In particular, in order to increase the productivity of the thin-film, a thin-film forming raw material that has a high vapor pressure is required. The related-art β-diketiminate metal complex is still insufficient in its vapor pressure, and hence a further improvement therein is required. In Patent Document 3, there is described a compound having a β-diketiminate ligand having one or more fluorine-containing organic groups, but the specific structure thereof is not described.

Solution to Problem

The inventors of the present invention have repeated extensive investigations, and as a result, have found that a compound having a β-diketiminate ligand having a group containing a fluorine atom at a specific position can solve the above-mentioned problem. Thus, the inventors have completed the present invention.

According to one embodiment of the present invention, there is provided a compound represented by the following formula (1).

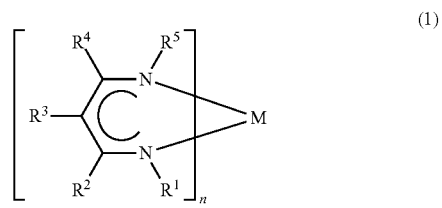

In the formula (1), $R^1$ to $R^5$ each independently represent a hydrogen atom, an alkyl group having 1 to 5 carbon atoms, or a group containing a fluorine atom, M represents a metal atom, and "n" represents a valence of the metal atom represented by M, provided that at least one of $R^2$, $R^3$, and $R^4$ represents the group containing a fluorine atom.

It is preferred that the group containing a fluorine atom represented by each of $R^1$ to $R^5$ in the formula (1) be an alkyl group having 1 to 5 carbon atoms substituted with a fluorine atom.

It is preferred that, in the formula (1), $R^1$ and $R^5$ each represent an alkyl group having 1 to 5 carbon atoms, at least one of $R^2$ and $R^4$ represent an alkyl group having 1 to 5 carbon atoms substituted with a fluorine atom, and $R^3$ represent a hydrogen atom.

It is preferred that M in the formula (1) represent a metal atom selected from copper, nickel, cobalt, tin, manganese, and zinc.

According to one embodiment of the present invention, there is provided a thin-film forming raw material, including the above-mentioned compound.

According to one embodiment of the present invention, there is provided a method of using the above-mentioned compound as a precursor for manufacturing a metal-containing thin-film by a chemical vapor deposition method.

According to one embodiment of the present invention, there is provided a thin-film, which is manufactured by using the above-mentioned method.

According to one embodiment of the present invention, there is provided a method of manufacturing a thin-film, including: introducing a raw material gas obtained by vaporizing the above-mentioned thin-film forming raw material into a treatment atmosphere having a substrate set therein; and subjecting the compound in the raw material gas to decomposition and/or a chemical reaction, to thereby form a metal-containing thin-film on a surface of the substrate.

Advantageous Effects of Invention

According to the present invention, the compound (β-diketiminate metal complex), which has a high vapor pressure and a low melting point, can be provided. With the thin-film forming raw material including the compound, a high-quality metal-containing thin-film can be formed by the CVD method, particularly the ALD method.

DESCRIPTION OF EMBODIMENTS

Figure 1:
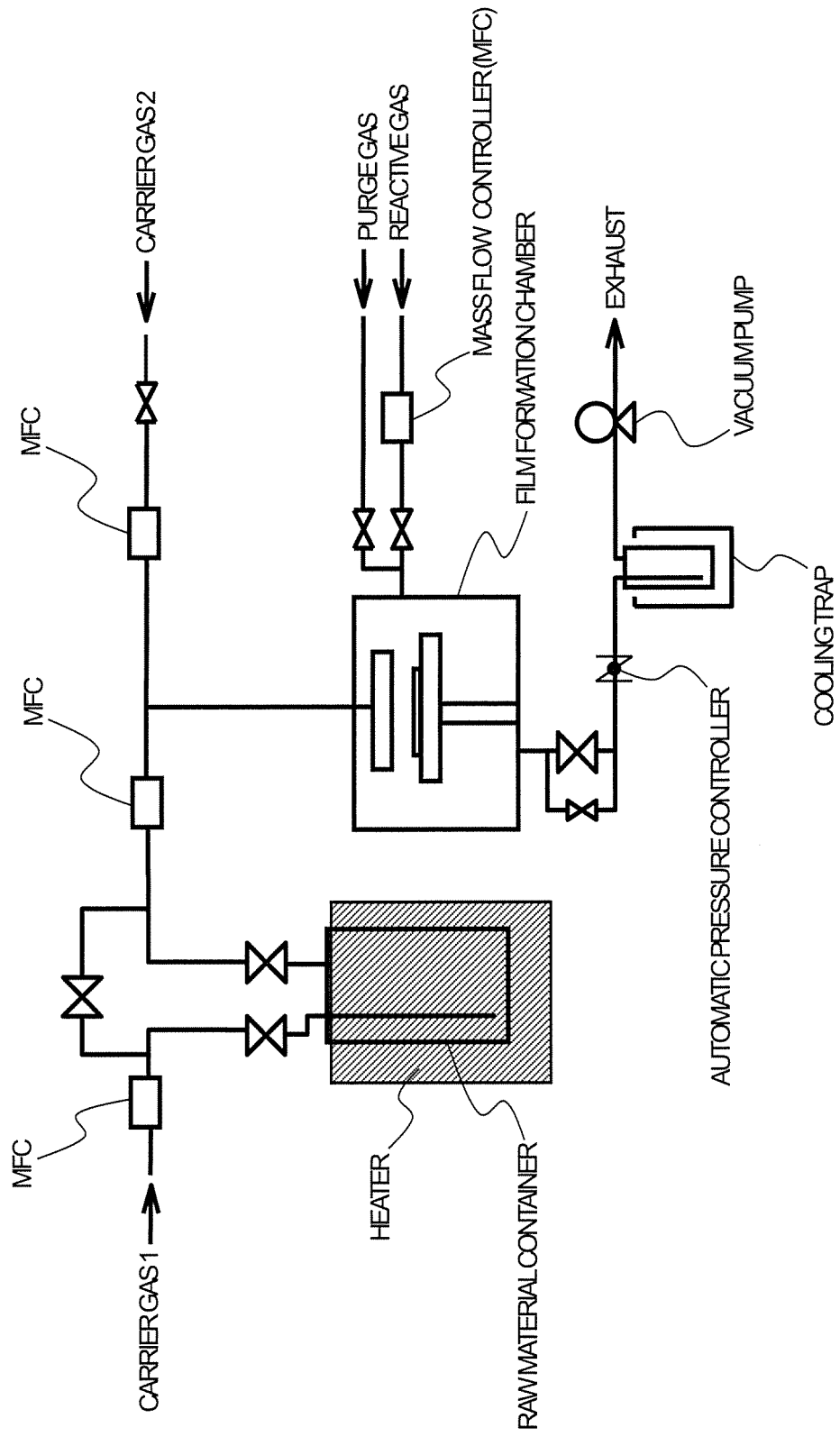
FIG. 1 is a schematic diagram for illustrating an example of an ALD apparatus to be used in a method of manufacturing a thin-film according to the present invention.

A compound of the present invention is represented by the following formula (1). The compound of the present invention is suitable as a precursor in a method of manufacturing a thin-film including a volatilization step, such as the ALD method, which is one kind of the CVD methods.

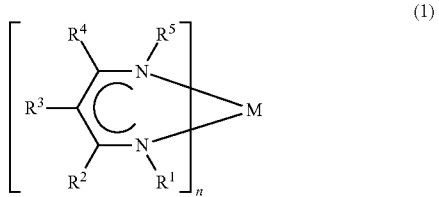

(1)

In the formula (1), $R^1$ to $R^5$ each independently represent a hydrogen atom, an alkyl group having 1 to 5 carbon atoms, or a group containing a fluorine atom, M represents a metal atom, and "n" represents a valence of the metal atom represented by M, provided that at least one of $R^2$, $R^3$, and $R^4$ represents the group containing a fluorine atom.

Examples of the alkyl group having 1 to 5 carbon atoms represented by each of $R^1$ to $R^5$ in the formula (1) include a methyl group, an ethyl group, a propyl group, an isopropyl group, a butyl group, a sec-butyl group, a tert-butyl group, an isobutyl group, a pentyl group, an isopentyl group, and a tert-pentyl group. Of those, from the viewpoint that a compound having a high vapor pressure is obtained, an alkyl group having 1 to 4 carbon atoms is preferred, a methyl group, an ethyl group, an isopropyl group, or a sec-butyl group is more preferred, and a methyl group or an ethyl group is still more preferred.

The group containing a fluorine atom represented by each of $R^1$ to $R^5$ in the formula (1) only needs to be one containing a fluorine atom, and may be a fluorine atom. Of those, from the viewpoint that the effect of the present invention becomes remarkable, an alkyl group having 1 to 5 carbon atoms substituted with a fluorine atom is preferred, a fluoroalkyl group, such as a fluoromethyl group, a difluoromethyl group, a trifluoromethyl group, a fluoroethyl group, a difluoroethyl group, a trifluoroethyl group, a fluoropropyl group, a difluoropropyl group, or a trifluoropropyl group, is more preferred, and a trifluoromethyl group is still more preferred.

Examples of the metal atom represented by M in the formula (1) include barium, titanium, zirconium, hafnium, vanadium, niobium, tantalum, chromium, molybdenum, tungsten, manganese, iron, osmium, ruthenium, cobalt, tin, rhodium, iridium, nickel, palladium, platinum, copper, silver, gold, zinc, aluminum, gallium, indium, germanium, lead, antimony, bismuth, radium, scandium, ruthenium, yttrium, lanthanum, cerium, praseodymium, neodymium, promethium, samarium, europium, gadolinium, terbium, dysprosium, holmium, erbium, thulium, ytterbium, and lutetium. Of those, from the viewpoint that the effect of the present invention becomes remarkable, M preferably represents a metal atom selected from copper, nickel, cobalt, tin, manganese, and zinc.

A compound in which, in the formula (1), $R^1$ and $R^5$ each represent an alkyl group having 1 to 5 carbon atoms, at least one of $R^2$ and $R^4$ represents an alkyl group having 1 to 5 carbon atoms substituted with a fluorine atom, and $R^3$ represents a hydrogen atom is preferred because the compound has a low melting point and high volatility, and can thus react with a reactive gas at low temperatures, to thereby form a metal-containing thin-film with good productivity. In particular, a compound in which $R^1$ and $R^5$ each represent a methyl group or an ethyl group, $R^2$ represents a trifluoromethyl group, $R^3$ represents a hydrogen atom, and $R^4$ represents a methyl group is more preferred because those effects become remarkable. Of those compounds, in particular, a compound in which M represents cobalt is still more preferred because the compound is a liquid at normal temperature.

Preferred specific examples of the compound of the present invention include the following compounds No. 1 to No. 48, but the present invention is not limited to those compounds. In the following compounds No. 1 to No. 48, "Me" represents a methyl group, "Et" represents an ethyl group, "iPr" represents an isopropyl group, "tBu" represents a tert-butyl group, "sBu" represents a sec-butyl group, and "$CF_3$" represents a trifluoromethyl group.

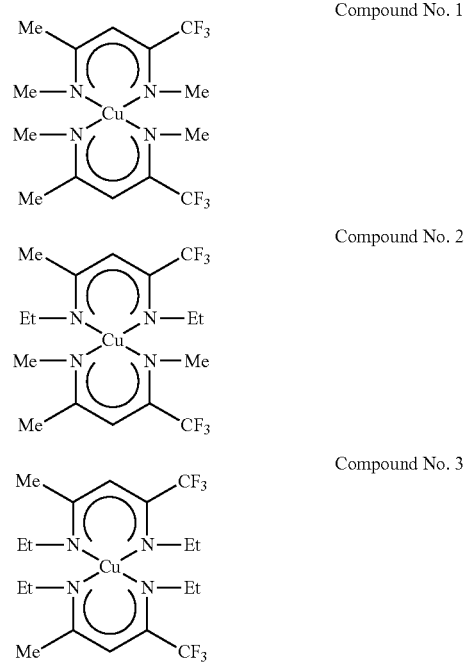

-continued
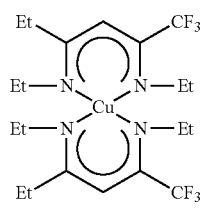
Compound No. 4
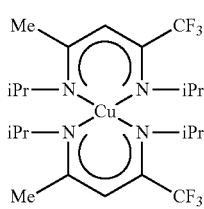
Compound No. 5
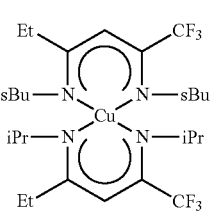
Compound No. 6
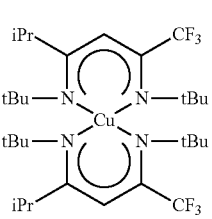
Compound No. 7
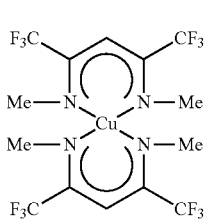
Compound No. 8
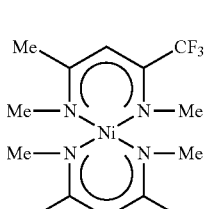
Compound No. 9
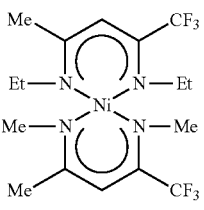
Compound No. 10
-continued
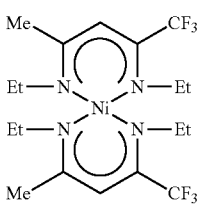
Compound No. 11
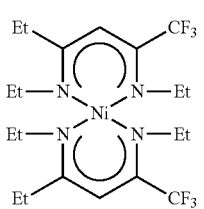
Compound No. 12
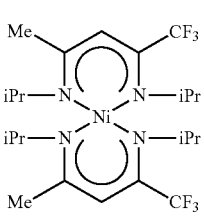
Compound No. 13
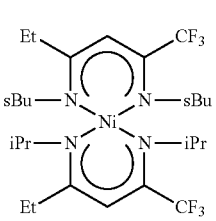
Compound No. 14
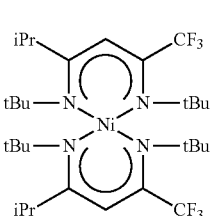
Compound No. 15
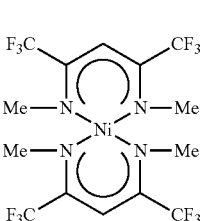
Compound No. 16
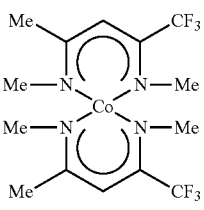
Compound No. 17

-continued
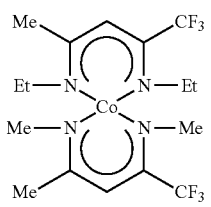
Compound No. 18
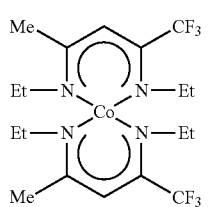
Compound No. 19
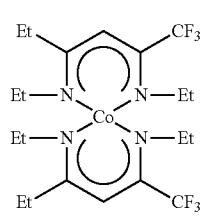
Compound No. 20
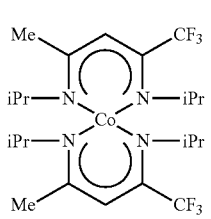
Compound No. 21
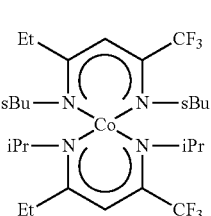
Compound No. 22
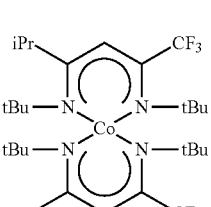
Compound No. 23
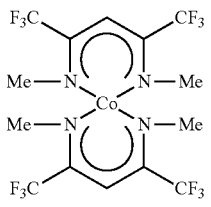
Compound No. 24
-continued
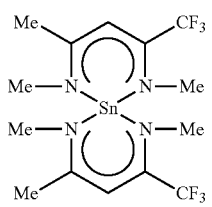
Compound No. 25
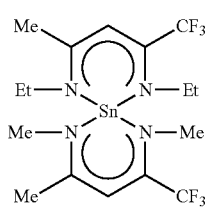
Compound No. 26
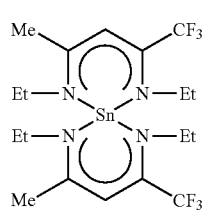
Compound No. 27
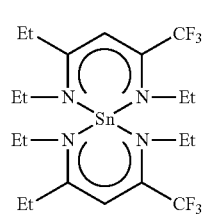
Compound No. 28
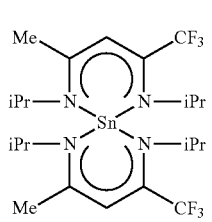
Compound No. 29
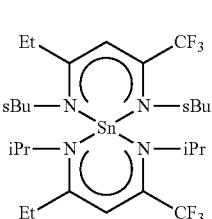
Compound No. 30
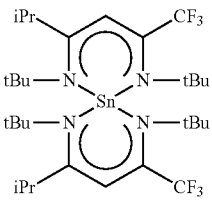
Compound No. 31

-continued
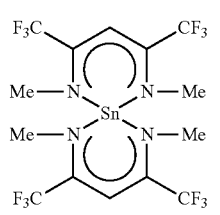 Compound No. 32
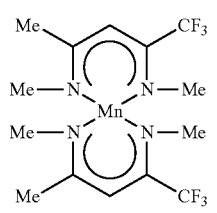 Compound No. 33
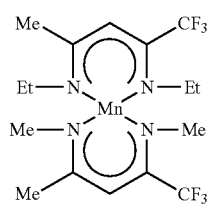 Compound No. 34
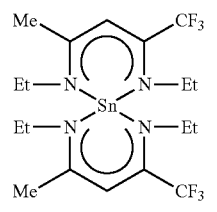 Compound No. 35
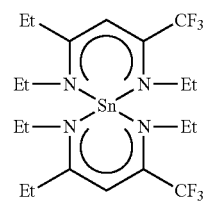 Compound No. 36
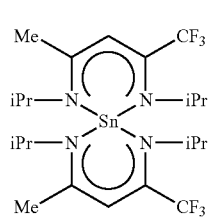 Compound No. 37
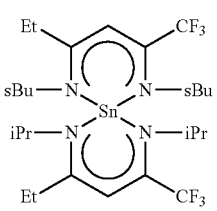 Compound No. 38
-continued
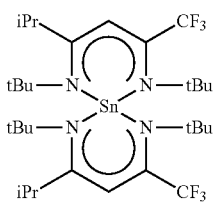 Compound No. 39
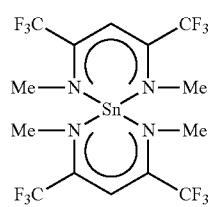 Compound No. 40
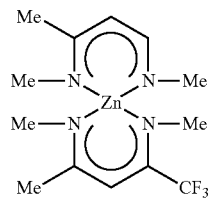 Compound No. 41
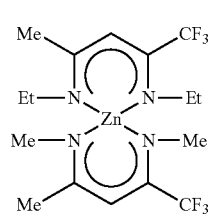 Compound No. 42
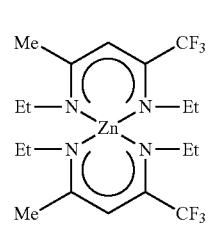 Compound No. 43
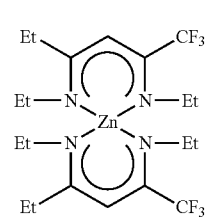 Compound No. 44
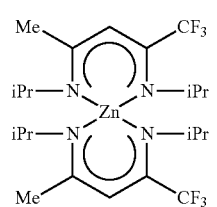 Compound No. 45

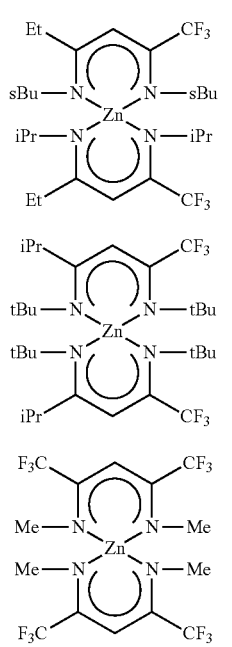

Compound No. 46

Compound No. 47

Compound No. 48

A method of manufacturing the compound represented by the formula (1) is not particularly limited, and the compound is manufactured by applying a well-known method. For example, a compound in which M represents copper may be obtained by dissolving copper methoxide in ethanol, adding a diketimine thereto to cause a reaction, removing the solvent, and performing distillation purification. In addition, the compound in which M represents cobalt may be obtained by dissolving cobalt bistrimethylsilylamide in toluene, adding a diketimine thereto to cause a reaction, removing the solvent, and performing distillation purification.

The compound of the present invention preferably has a melting point of less than 100° C., and is more preferably a liquid at normal temperature in order to ensure, in a film formation apparatus for manufacturing a thin-film through use of the compound of the present invention, transportability in piping of the film formation apparatus.

Next, a thin-film forming raw material of the present invention is described.

The thin-film forming raw material of the present invention only needs to include the compound represented by the formula (1) and use the compound as a precursor of a thin-film, and the composition thereof varies depending on the kind of a target thin-film. For example, when a thin-film containing only a single metal as a metal is to be manufactured, the thin-film forming raw material of the present invention is free of a metal compound other than the metal and a semimetal compound. Meanwhile, when a thin-film containing a plurality of metals and/or semimetals is to be manufactured, the thin-film forming raw material of the present invention may include a compound containing a desired metal and/or a compound containing a semimetal (hereinafter referred to as "other precursor") in addition to the compound represented by the formula (1).

In addition, in the case of a multi-component CVD method in which a plurality of precursors are used, there is no particular limitation on the other precursor that may be used with the compound represented by the formula (1), and a well-known general precursor used for the thin-film forming raw material for a CVD method may be used.

Examples of the above-mentioned other precursor include compounds each containing: one kind or two or more kinds selected from the group consisting of compounds used as organic ligands, such as an alcohol compound, a glycol compound, a β-diketone compound, a cyclopentadiene compound, and an organic amine compound; and silicon or a metal. In addition, examples of the kind of the metal in the precursor include lithium, sodium, potassium, magnesium, calcium, strontium, barium, titanium, zirconium, hafnium, vanadium, niobium, tantalum, chromium, molybdenum, tungsten, manganese, iron, osmium, ruthenium, cobalt, rhodium, iridium, nickel, palladium, platinum, copper, silver, gold, zinc, aluminum, gallium, indium, germanium, lead, antimony, bismuth, radium, scandium, ruthenium, yttrium, lanthanum, cerium, praseodymium, neodymium, promethium, samarium, europium, gadolinium, terbium, dysprosium, holmium, erbium, thulium, ytterbium, and lutetium.

Examples of the alcohol compound to be used as the organic ligand in the above-mentioned other precursor include: alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; and dialkylamino alcohols, such as dimethylaminoethanol, ethylmethylaminoethanol, diethylaminoethanol, dimethylamino-2-pentanol, ethylmethylamino-2-pentanol, dimethylamino-2-methyl-2-pentanol, ethylmethylamino-2-methyl-2-pentanol, and diethylamino-2-methyl-2-pentanol.

Examples of the glycol compound to be used as the organic ligand in the above-mentioned other precursor include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compound to be used as the organic ligand in the above-mentioned other precursor include: alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted alkyl β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compound to be used as the organic ligand in the above-mentioned other precursor include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene.

Examples of the organic amine compound to be used as the organic ligand in the above-mentioned other precursor include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

The above-mentioned other precursors are known in the art, and production methods therefor are also known. One example of the production methods is given as described below. For example, when the alcohol compound is used as the organic ligand, the precursor may be manufactured through a reaction between an inorganic salt of the metal described above or a hydrate thereof and an alkali metal alkoxide of the alcohol compound. In this case, examples of the inorganic salt of the metal or the hydrate thereof may include a halide and a nitrate of the metal. Examples of the alkali metal alkoxide may include a sodium alkoxide, a lithium alkoxide, and a potassium alkoxide.

In the multi-component CVD method as described above, there are adopted: a method involving vaporizing and supplying each component of the thin-film forming raw material independently (hereinafter referred to as "single source method"); and a method involving vaporizing and supplying a mixed raw material obtained by mixing multi-component raw materials in accordance with desired composition in advance (hereinafter referred to as "cocktail source method"). In the case of the single source method, the above-mentioned other precursor is preferably a compound similar to the compound represented by the formula (1) in the behavior of thermal decomposition and/or oxidative decomposition. In the case of the cocktail source method, the above-mentioned other precursor is preferably a compound that not only is similar to the compound represented by the formula (1) in the behavior of thermal decomposition and/or oxidative decomposition but also is prevented from being altered through a chemical reaction or the like at the time of mixing with the compound represented by the formula (1).

In addition, in the case of the cocktail source method in the multi-component CVD method, a mixture of the compound represented by the formula (1) and the other precursor, or a mixed solution obtained by dissolving the mixture in an organic solvent may be used as the thin-film forming raw material.

There is no particular limitation on the above-mentioned organic solvent, and a well-known general organic solvent may be used. Examples of the organic solvent include: acetic acid esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl pentyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons each having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; and pyridine and lutidine. Those organic solvents may be used alone or as a mixture thereof depending on the solubility of a solute, the relationship among the use temperature, boiling point, and flash point of the solvent, and the like.

When the thin-film forming raw material of the present invention is the mixed solution with the organic solvent, the amount of the entire precursors in the thin-film forming raw material is preferably from 0.01 mol/liter to 2.0 mol/liter, more preferably from 0.05 mol/liter to 1.0 mol/liter.

Herein, when the thin-film forming raw material of the present invention is free of a metal compound other than the compound represented by the formula (1) and a semimetal compound, the amount of the entire precursors refers to the amount of the compound represented by the formula (1). When the thin-film forming raw material of the present invention includes a compound containing another metal and/or a compound containing a semimetal (other precursor) in addition to the compound represented by the formula (1), the amount of the entire precursors refers to the total amount of the compound represented by the formula (1) and the other precursor.

In addition, the thin-film forming raw material of the present invention may include a nucleophilic reagent as required in order to improve the stability of each of the compound represented by the formula (1) and the other precursor. Examples of the nucleophilic reagent include: ethylene glycol ethers, such as glyme, diglyme, triglyme, and tetraglyme; crown ethers, such as 18-crown-6, dicyclohexyl-18-crown-6,24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, 3,5-heptanedione, and dipivaloylmethane. The usage amount of each of those nucleophilic reagents falls within the range of preferably from 0.1 mol to 10 mol, more preferably from 1 mol to 4 mol with respect to 1 mol of the amount of the entire precursors.

It is desired that the thin-film forming raw material of the present invention be prevented from including impurity metal elements other than the components for forming the raw material, impurity halogens, such as impurity chlorine, and impurity organic substances to the extent possible. The content of each of the impurity metal elements is preferably 100 ppb or less, more preferably 10 ppb or less, and the total content thereof is preferably 1 ppm or less, more preferably 100 ppb or less. In particular, when the raw material is used as a gate insulating film, a gate film, or a barrier layer of an LSI, it is required to reduce the contents of alkali metal elements and alkaline-earth metal elements that influence the electrical characteristics of a thin-film to be obtained. The content of the impurity halogens is preferably 100 ppm or less, more preferably 10 ppm or less, still more preferably 1 ppm or less. The total content of the impurity organic substances is preferably 500 ppm or less, more preferably 50 ppm or less, still more preferably 10 ppm or less. In addition, moisture causes generation of particles in the thin-film forming raw material and generation of particles during thin-film formation. Accordingly, in order to reduce moisture in each of the precursor, the organic solvent, and the nucleophilic reagent, the moisture is desirably removed as much as possible in advance at the time of use. The moisture content of each of the precursor, the organic solvent, and the nucleophilic reagent is preferably 10 ppm or less, more preferably 1 ppm or less.

In addition, it is preferred that the thin-film forming raw material of the present invention be prevented from including particles to the extent possible in order to reduce or prevent particle contamination of a thin-film to be formed. Specifically, in particle measurement with a light scattering liquid particle detector in a liquid phase, it is preferred that the number of particles larger than 0.3 µm be 100 or less in 1 ml of the liquid phase, and it is more preferred that the number of particles larger than 0.2 µm be 100 or less in 1 ml of the liquid phase.

Next, a method of manufacturing a thin-film of the present invention by using the thin-film forming raw material is described.

In the method of manufacturing a thin-film of the present invention, a well-known ALD apparatus may be used. As specific examples of the ALD apparatus, there are given an apparatus capable of performing bubbling supply of a precursor as illustrated in each of FIG. 1 and FIG. 3, and an apparatus including a vaporization chamber as illustrated in each of FIG. 2 and FIG. 4. In addition, there is given an apparatus capable of subjecting a reactive gas to plasma treatment as illustrated in each of FIG. 3 and FIG. 4. The apparatus is not limited to a single-substrate type apparatus including a film formation chamber (hereinafter referred to as "deposition reaction portion") as illustrated in each of FIG. 1 to FIG. 4, and an apparatus capable of simultaneously processing a large number of substrates through use of a batch furnace may also be used. Those apparatus may also be each used as a CVD apparatus.

The method of manufacturing a thin-film of the present invention includes: a step (raw material gas introduction step) of introducing a raw material gas obtained by vaporizing the above-mentioned thin-film forming raw material into a deposition reaction portion (treatment atmosphere); a step (precursor thin-film formation step) of depositing the metal compound in the raw material gas on the surface of a substrate, to thereby form a precursor thin-film; and a step (metal-containing thin-film formation step) of introducing a reactive gas into the deposition reaction portion (treatment atmosphere) to cause the precursor thin-film and the reactive gas to react with each other, to thereby form a metal-containing thin-film on the surface of the substrate. In addition, the method of manufacturing a thin-film of the present invention preferably includes a step (evacuation step) of evacuating a gas in the deposition reaction portion (treatment atmosphere) between the precursor thin-film formation step and the metal-containing thin-film formation step and/or after the metal-containing thin-film formation step.

In one embodiment of the method of manufacturing a thin-film of the present invention, when deposition performed by a series of operations in which the precursor thin-film formation step, the evacuation step, the metal-containing thin-film formation step, and the evacuation step are performed in the stated order is defined as one cycle, and the cycle is repeated, the thickness of the thin-film of the present invention can be adjusted. Now, each of the steps of the method of manufacturing a thin-film of the present invention is described.

Raw Material Gas Introduction Step

The raw material gas introduction step is a step of vaporizing the above-mentioned thin-film forming raw material to obtain vapor (hereinafter referred to as "raw material gas"), and introducing the raw material gas into a film formation chamber having a substrate set therein.

As a transportation and supply method for the thin-film forming raw material, there are given a gas transportation method involving heating and/or decompressing the thin-film forming raw material of the present invention in a container in which the raw material is stored (hereinafter referred to as "raw material container"), to thereby vaporize the raw material to obtain vapor, and introducing the vapor into a deposition reaction portion having a substrate set therein together with a carrier gas, such as argon, nitrogen, or helium, as required as illustrated in each of FIG. 1 and FIG. 3, and a liquid transportation method involving transporting the thin-film forming raw material under the state of a liquid or a solution to a vaporization chamber, heating and/or decompressing the raw material in the vaporization chamber, to thereby vaporize the raw material to obtain vapor, and introducing the vapor as a raw material gas to the deposition reaction portion as illustrated in each of FIG. 2 and FIG. 4. In the case of the gas transportation method, the compound represented by the formula (1) itself may be used as the thin-film forming raw material. In the case of the liquid transportation method, the compound represented by the formula (1) or a solution obtained by dissolving the compound in an organic solvent may be used as the thin-film forming raw material. Such mixture or mixed solution may further contain a nucleophilic reagent or the like.

In addition, as other methods to be used in the raw material gas introduction step than the gas transportation method and the liquid transportation method, there are given the single source method and the cocktail source method, which have been described in the "Thin-film Forming Raw material" section as multi-component ALD methods including a plurality of precursors. Regardless of which introduction method is used, the thin-film forming raw material of the present invention is preferably vaporized at a temperature of from 0° C. to 200° C. In addition, when the thin-film forming raw material is vaporized to obtain vapor in the raw material container or in the vaporization chamber, the pressure in the raw material container and the pressure in the vaporization chamber preferably fall within the range of from 1 Pa to 10,000 Pa.

Herein, as a material for the substrate to be set in the deposition reaction portion, there are given, for example: silicon; ceramics, such as silicon nitride, titanium nitride, tantalum nitride, titanium oxide, ruthenium oxide, zirconium oxide, hafnium oxide, and lanthanum oxide; glass; and metals, such as metal cobalt and metal ruthenium. The shape of the substrate is, for example, a plate shape, a spherical shape, a fibrous shape, or a scaly shape. The surface of the substrate may be planar, or may have a three-dimensional structure, such as a trench structure.

Precursor Thin-Film Formation Step

In the precursor thin-film formation step, the compound represented by the formula (1) in the raw material gas introduced into the deposition reaction portion having the substrate set therein is deposited on the surface of the substrate, to thereby form the precursor thin-film on the surface of the substrate. At this time, heat may be applied by heating the substrate or heating the deposition reaction portion. There are no particular limitations on the production conditions under which the precursor thin-film is formed, but for example, a reaction temperature (substrate temperature), a reaction pressure, a deposition rate, and the like may appropriately be determined depending on the kind of the thin-film forming raw material. The reaction temperature is preferably not less than 100° C. that is the temperature at which the thin-film forming raw material of the present invention sufficiently reacts, more preferably from 100° C. to 400° C. The reaction pressure is preferably from 1 Pa to 10,000 Pa, more preferably from 10 Pa to 1,000 Pa.

In addition, the deposition rate may be controlled by the supply conditions (vaporization temperature and vaporization pressure) of the thin-film forming raw material, the reaction temperature, and the reaction pressure. When the deposition rate is high, the characteristics of a thin-film to be obtained may deteriorate. When the deposition rate is low, a problem may occur in productivity. Accordingly, the deposition rate is preferably from 0.01 nm/min to 100 nm/min, more preferably from 0.1 nm/min to 50 nm/min.

Evacuation Step

After the precursor thin-film has been formed, the raw material gas not having been deposited on the surface of the substrate is evacuated from the deposition reaction portion. At this time, it is ideal that the raw material gas be completely evacuated from the deposition reaction portion, but it is not always required that the gas be completely evacuated. As an evacuation method, there are given, for example, a method involving purging the inside of the system of the deposition reaction portion with an inert gas, such as helium, nitrogen, or argon, a method involving performing evacuation by decompressing the inside of the system, and a combination of these methods. The degree of decompression in the case of performing decompression falls within the range of preferably from 0.01 Pa to 300 Pa, more preferably from 0.01 Pa to 100 Pa.

Metal-Containing Thin-Film Formation Step

In the metal-containing thin-film formation step, the reactive gas is introduced into the deposition reaction portion after the evacuation step so that the reactive gas is caused to react with the precursor thin-film, that is, the compound represented by the formula (1) having been deposited on the surface of the substrate through the action of the reactive gas or through the action of the reactive gas and the action of heat, to thereby form the metal-containing thin-film.

Examples of the reactive gas include: oxidizing gases, such as oxygen, ozone, nitrogen dioxide, nitrogen monoxide, water vapor, hydrogen peroxide, formic acid, acetic acid, and acetic anhydride; reducing gases, such as hydrogen; organic amine compounds, such as a monoalkylamine, a dialkylamine, a trialkylamine, and an alkylenediamine; and nitriding gases, such as hydrazine and ammonia. Those reactive gases may be used alone or as a mixture thereof.

When heat is used in the reaction between the precursor thin-film and the reactive gas, the temperature thereof is preferably from 50° C. to 200° C., more preferably from 100° C. to 200° C. In addition, the pressure in the deposition reaction portion when this step is performed is preferably from 1 Pa to 10,000 Pa, more preferably from 10 Pa to 1,000 Pa.

Evacuation Step

After the metal-containing thin-film formation step, an unreacted reactive gas and a by-product gas are evacuated from the deposition reaction portion. At this time, it is ideal that the reactive gas and the by-product gas be completely evacuated from the deposition reaction portion, but it is not always required that the gases be completely evacuated. An evacuation method and the degree of decompression in the case of performing decompression are the same as those in the above-mentioned evacuation step after the precursor thin-film formation step.

As described above, when deposition performed by a series of operations in which the raw material gas introduction step, the precursor thin-film formation step, the evacuation step, the metal-containing thin-film formation step, and the evacuation step are performed in the stated order is defined as one cycle, and the cycle is repeated a plurality of times until a thin-film having a required film thickness is obtained, a metal-containing thin-film having a desired film thickness is manufactured. In the method of manufacturing a thin-film by the ALD method, the film thickness of the metal-containing thin-film to be formed can be controlled by the number of the cycles.

Figure 3:
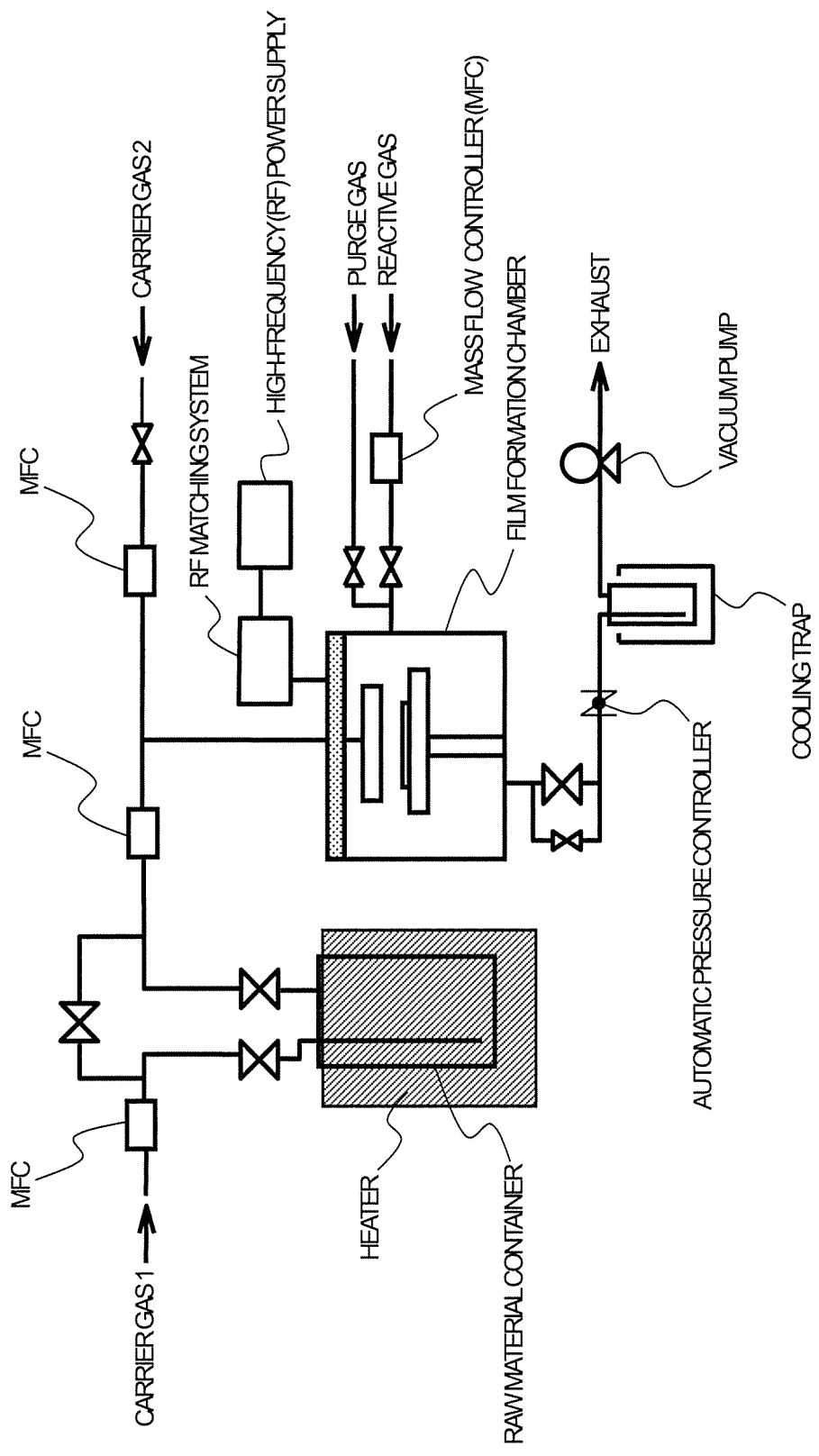
FIG. 3 is a schematic diagram for illustrating still another example of the ALD apparatus to be used in the method of manufacturing a thin-film according to the present invention.
Figure 4:
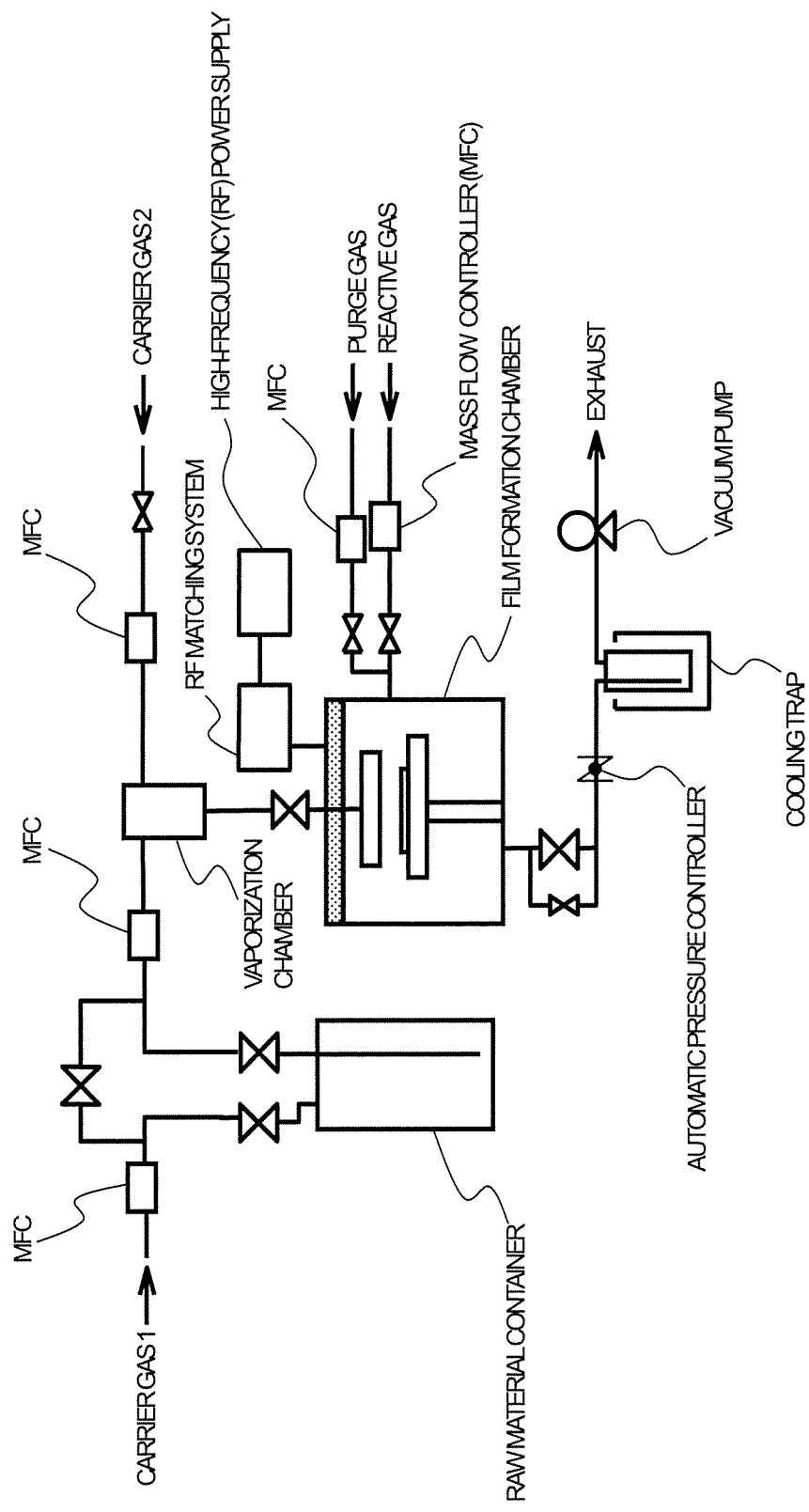
FIG. 4 is a schematic diagram for illustrating yet still another example of the ALD apparatus to be used in the method of manufacturing a thin-film according to the present invention.

In addition, in the method of manufacturing a thin-film of the present invention, as illustrated in each of FIG. 3 and FIG. 4, energy, such as plasma, light, or a voltage, may be applied to the deposition reaction portion, or a catalyst may be used. There are no particular limitations on the timing for applying the energy and the timing for using the catalyst. The energy may be applied or the catalyst may be used, for example, at the time of introducing the raw material gas of the thin-film forming raw material in the raw material gas introduction step, at the time of a heating step in the precursor thin-film formation, at the time of introducing the reactive gas or at the time of causing the reactive gas and the precursor thin-film to react with each other in the metal-containing thin-film formation step, or at the time of evacuating the inside of the system in the evacuation step, or between the above-mentioned respective steps.

In addition, in the method of manufacturing a thin-film of the present invention, after the formation of the thin-film, annealing treatment may be performed under an inert atmosphere, an oxidizing atmosphere, or a reducing atmosphere in order to obtain more satisfactory electrical characteristics. When step embedding is required, a reflow step may be provided. The temperature of the atmosphere in this case is preferably from 200° C. to 1,000° C., more preferably from 250° C. to 500° C.

The thin-film to be manufactured by using the thin-film forming raw material of the present invention may be formed as a desired kind of thin-film, which covers a substrate formed of, for example, a metal, an oxide ceramic, a nitride ceramic, or glass, by appropriately selecting the other precursor, the reactive gas, and the production conditions. The thin-film of the present invention is excellent in electrical characteristics and optical characteristics, and hence can be widely used in the production of, for example, electrode materials for memory elements typified by DRAM elements, resistance films, diamagnetic films used for the recording layers of hard disks, and catalyst materials for polymer electrolyte fuel cells.

EXAMPLES

The present invention is described in more detail below by way of Examples and the like. However, the present invention is by no means limited by Examples and the like below.

Example 1

Synthesis of Compound No. 1

Figure 5:
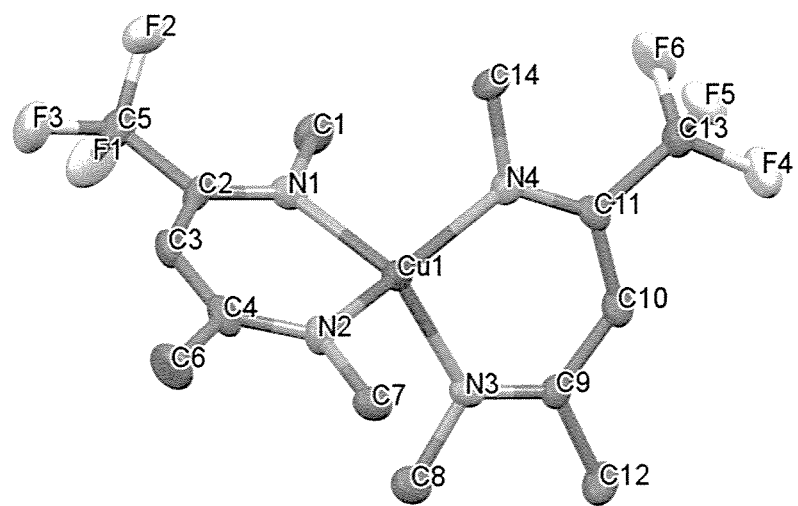
FIG. 5 is a molecular structure diagram of Compound No. 1 by single crystal X-ray analysis.

0.60 g (4.7 mmol) of a copper(II) methoxide complex and 20 ml of dehydrated ethanol were loaded into a 100-milliliter four-necked flask at room temperature. 1.69 g (9.4 mmol) of a corresponding diketimine ligand was added dropwise thereto under cooling with ice, and the mixture was stirred at room temperature for 20 hours. Ethanol was distilled away in an oil bath at 75° C. under slightly reduced pressure. After that, a purple solid remaining in the flask was distilled under reduced pressure (50 Pa), and 0.92 g (2.2 mmol, yield: 46%) of the purple solid was obtained as a distillate. The solid was analyzed by single crystal X-ray analysis, and as a result, was identified as Compound No. 1, which was a target compound. The molecular structure of the resultant purple solid by the single crystal X-ray analysis is shown in FIG. 5.

Results of Single Crystal X-Ray Analysis of Compound No. 1

Crystal lattice size: 0.11 mm×0.11 mm×0.10 mm
Crystal system: triclinic system
(Two molecules in an asymmetric unit, R1=0.0820, wR2=0.1807)
Lattice parameters:
a=8.859 Å
b=9.349 Å
c=12.58 Å
$\alpha$=74.69°
$\beta$=71.28°
$\gamma$=63.91°
V=877 Å$^3$

Example 2

Synthesis of Compound No. 19

Figure 6:
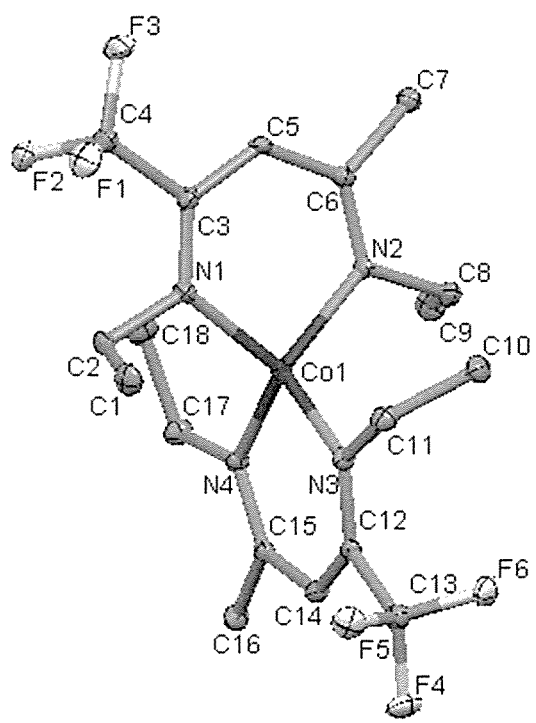
FIG. 6 is a molecular structure diagram of Compound No. 19 by single crystal X-ray analysis.

8.4 g (22.2 mmol) of a cobalt bistrimethylsilylamide complex and 50 ml of dehydrated toluene were loaded into a 100-milliliter four-necked flask at room temperature. 6.8 g (44.4 mmol) of a corresponding diketimine ligand was added dropwise thereto at room temperature, and a reaction was performed for 2 hours. The toluene solvent was distilled away in an oil bath at 100° C. under slightly reduced pressure. After that, a dark brown viscos liquid remaining in the flask was distilled under reduced pressure (from 20 Pa to 30 Pa), and 7.5 g (20.5 mmol, yield: 92.4%) of a dark reddish brown liquid was obtained as a distillate. The resultant dark reddish brown liquid slowly solidified at room temperature to become a dark reddish brown solid having a melting point of 38° C. The solid was analyzed by single crystal X-ray analysis, and as a result, was identified as Compound No. 19, which was a target compound. The molecular structure of the resultant dark reddish brown solid by the single crystal X-ray analysis is shown in FIG. 6.

Results of Single Crystal X-Ray Analysis of Compound No. 19

Crystal lattice size: 0.26 mm×0.24 mm×0.07 mm
Crystal system: monoclinic system
(Eight molecules in an asymmetric unit, R1=0.0598, wR2=0.1310)
Lattice parameters:
a=28.047 Å
b=9.9896 Å
c=18.954 Å
$\beta$=125.704°
V=4,312 Å$^3$

Example 3

Synthesis of Compound No. 27

1.65 g (3.8 mmol) of a tin bistrimethylsilylamide complex and 25 ml of dehydrated hexane were loaded into a 100-milliliter four-necked flask at room temperature. 1.58 g (7.6 mmol) of a corresponding diketimine ligand was added dropwise thereto under cooling with ice, and a reaction was performed for 16 hours. The hexane solvent was distilled away in an oil bath at 60° C. under slightly reduced pressure. After that, an orange liquid remaining in the flask was distilled under reduced pressure (from 20 Pa to 30 Pa), and 0.05 g (0.1 mmol, yield: 2.5%) of a yellow solid was obtained as a distillate. The yellow solid was analyzed by $^1$H-NMR and ICP-AES, and as a result, was identified as Compound No. 27, which was a target compound. The analysis results of the resultant yellow solid by $^1$H-NMR and ICP-AES are shown below.

Analysis Results by $^1$H-NMR (Deuterated Benzene)

0.868 ppm to 0.904 ppm (3H, triplet), 1.147 ppm to 1.183 ppm (3H, triplet), 1.563 ppm (3H, singlet), 3.049 ppm to 3.067 ppm (2H, doublet), 3.585 ppm (2H, singlet), 5.166 ppm (1H, singlet)

Analysis Results by ICP-AES

Content of tin: 22.1 mass % (theoretical value: 22.27 mass %)

Example 4

Synthesis of Compound No. 43

0.57 g (4.2 mmol) of a zinc chloride complex and 40 ml of an ether were loaded into a 100-milliliter four-necked flask at room temperature. 1.93 g (8.4 mmol) of a corresponding lithiated diketimine ligand was added dropwise thereto under cooling with ice, and a reaction was performed for 16 hours. The ether solution was distilled away in an oil bath at 50° C. under normal pressure. Hexane was added to the resultant yellow solid, followed by filtration. The solvent was removed from the filtrate in an oil bath at 60° C. under slightly reduced pressure. After that, an orange liquid remaining in the flask was distilled under reduced pressure (from 20 Pa to 30 Pa), and 1.18 g (2.5 mmol, yield: 59%) of a pale yellow liquid was obtained as a distillate. The pale yellow liquid was analyzed by $^1$H-NMR and ICP-AES, and as a result, was identified as Compound No. 43, which was a target compound. The analysis results of the resultant pale yellow liquid by $^1$H-NMR and ICP-AES are shown below.

Analysis Results by $^1$H-NMR (Deuterated Benzene)

0.889 ppm to 0.925 ppm (3H, triplet), 1.079 ppm to 1.115 ppm (3H, triplet), 1.547 ppm (3H, singlet), 2.977 ppm to 3.043 ppm (2H, multiplet), 3.502 ppm to 3.557 ppm (2H, multiplet), 5.008 ppm (1H, singlet)

Analysis Results by ICP-AES

Content of zinc: 13.8 mass % (theoretical value: 13.63 mass %)

Comparative Example 1

Synthesis of Comparative Compound 1

The following Comparative Compound 1, in which, in the formula (1), $R^1$ and $R^5$ each represented $CH_2CF_3$, $R^2$ and $R^4$ each represented Me, $R^3$ represented H, and M represented Cu, was tried to be synthesized.

1.07 g (8.5 mmol) of a copper(II) methoxide complex and 50 ml of dehydrated ethanol were loaded into a 100-milliliter four-necked flask at room temperature. 4.46 g (17 mmol) of a diketimine ligand corresponding to the following Comparative Compound 1 was added dropwise thereto under cooling with ice, and the mixture was stirred at room temperature for 18 hours. Ethanol was distilled away in an oil bath at 75° C. under slightly reduced pressure. After that, a black solid remaining in the flask was distilled under reduced pressure (50 Pa), but the target was not able to be isolated.

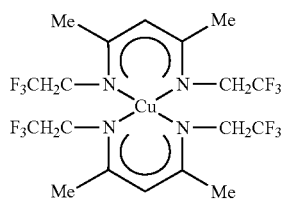

Comparative Compound 1

Evaluation Example

The following evaluations were performed by using Compound No. 1, Compound No. 19, Compound No. 27, and Compound No. 43 obtained through the synthesis in Examples 1 to 4 described above, respectively, and Comparative Compounds 2 to 5 shown in Tables 1 to 4 below.

(1) Evaluation of Melting Point

The state of each of the compounds at normal pressure and 25° C. was visually observed, and when the compound was a solid, its melting point was measured with a micro melting point meter. The results are shown in Tables 1 to 4.

(2) Temperature (° C.) at Reduced Pressure TG-DTA 50 Mass % Reduction

Measurement was performed with a TG-DTA at 10 Torr, an Ar flow rate of 50 mL/min, and a temperature increase rate of 10° C./min in a scanning temperature range of from 30° C. to 600° C. A temperature (° C.) at which the weight of a test compound was reduced by 50 mass % was evaluated as a "temperature (° C.) at reduced pressure TG-DTA 50 mass % reduction." A lower temperature (° C.) at reduced pressure TG-DTA 50 mass % reduction indicates that vapor is obtained at lower temperatures. The results are shown in Tables 1 to 4.

TABLE 1

| Compound | Example 1<br>Compound No. 1 | Comparative Example 2<br>Comparative Compound 2 |
|---|---|---|
| Molecular weight | 421 | 314 |
| Melting point [° C.] | 130 | 177 |
| Temperature [° C.] at reduced pressure TG-DTA 50 mass % reduction | 138 | 173 |

TABLE 2

| Compound | Example 2<br>Compound No. 19 | Comparative Example 3<br>Comparative Compound 3 |
|---|---|---|
| Molecular weight | 478 | 365 |
| Melting point [° C.] | 38 | 42 |
| Temperature [° C.] at reduced pressure TG-DTA 50 mass % reduction | 140 | 162 |

TABLE 3

| Compound | Example 3<br>Compound No. 27 | Comparative Example 4<br>Comparative Compound 4 |
|---|---|---|
| Molecular weight | 533 | 369 |

TABLE 3-continued

| | Example 3<br>Compound No. 27 | Comparative<br>Example 4<br>Comparative<br>Compound 4 |
|---|---|---|
| Compound | Me, CF₃ / Et—N, N—Et / Sn / Et—N, N—Et / Me, CF₃ | Me, Me / Me—N, N—Me / Sn / Me—N, N—Me / Me, Me |
| Melting point [° C.] | 124 | 104 |
| Temperature [° C.] at reduced pressure TG-DTA 50 mass % reduction | 131 | 163 |

TABLE 4

| | Example 4<br>Compound No. 43 | Comparative<br>Example 5<br>Comparative<br>Compound 5 |
|---|---|---|
| Compound | Me, CF₃ / Et—N, N—Et / Zn / Et—N, N—Et / Me, CF₃ | Me, Me / Me—N, N—Me / Zn / Me—N, N—Me / Me, Me |
| Molecular weight | 480 | 316 |
| Melting point [° C.] | Liquid | 151 |
| Temperature [° C.] at reduced pressure TG-DTA 50 mass % reduction | 138 | 155 |

Example 5

Figure 2:
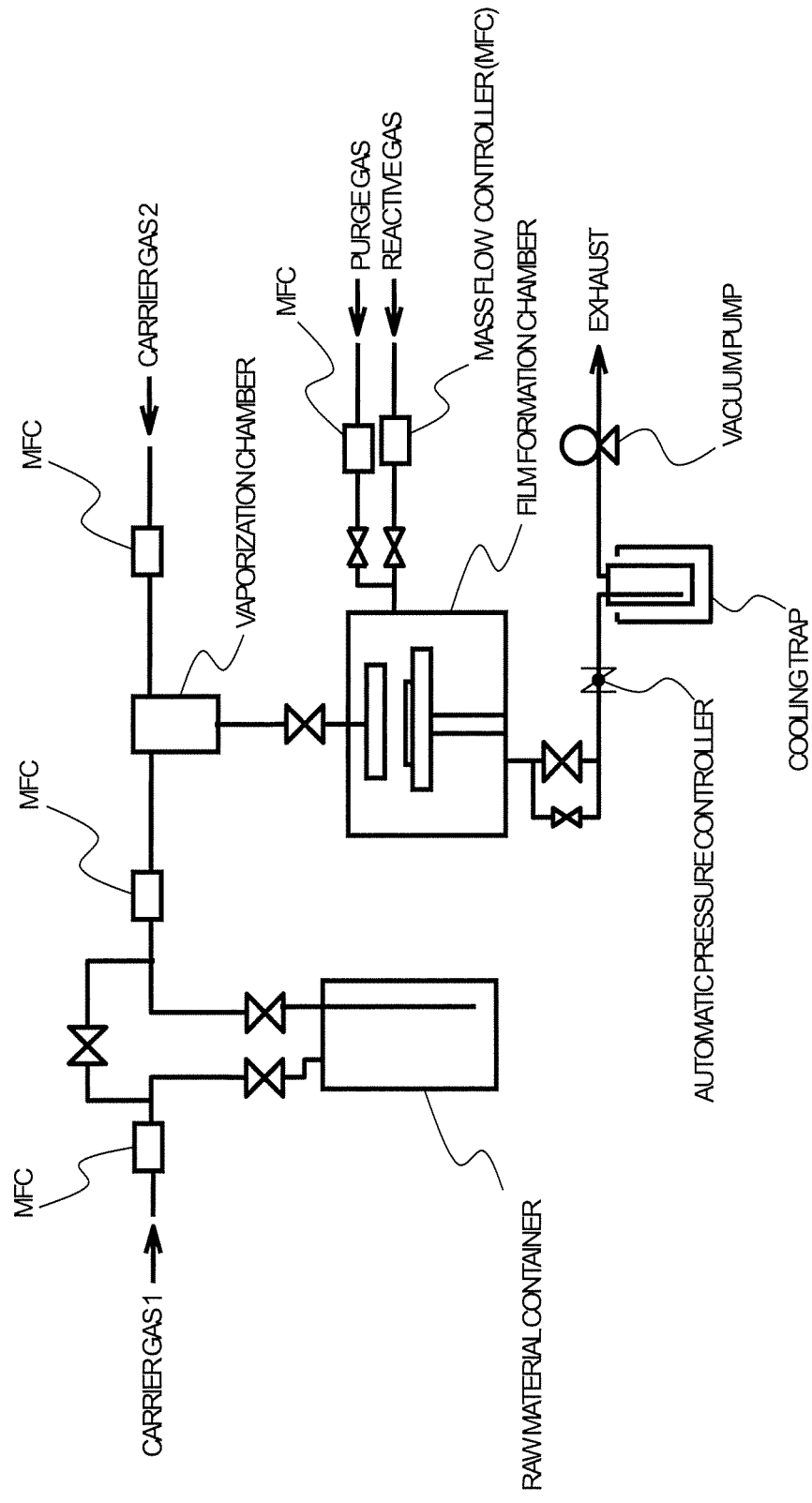
FIG. 2 is a schematic diagram for illustrating another example of the ALD apparatus to be used in the method of manufacturing a thin-film according to the present invention.

A thin-film was manufactured on the surface of a ruthenium wafer serving as a substrate under the following conditions with an ALD apparatus of FIG. 1 by using Compound No. 1 as a thin-film forming raw material. When the composition of the thin-film was analyzed by X-ray photoelectron spectroscopy, it was recognized that the thin-film was a thin-film containing copper, and the content of residual carbon was less than 0.1 atom %, which was a detection limit. In addition, when the film thickness of the thin-film was measured by scanning electron microscopy, the thin-film formed on the surface of the ruthenium wafer was a smooth and flat film having a film thickness of 2 nm, and the film thickness obtained per cycle was about 0.02 nm.

Production Conditions

Production method: ALD method
Reaction temperature (substrate temperature): 200° C.
Reactive gas: hydrogen Steps A series of steps consisting of the following (1) to (4) was defined as one cycle, and this cycle was repeated 100 times.
(1) A precursor thin-film is formed by introducing vapor (raw material gas) of the thin-film forming raw material obtained through vaporization under the conditions of a raw material container temperature of 120° C. and a raw material container internal pressure of 100 Pa into a deposition reaction portion, and depositing the raw material gas on the surface of a substrate at a system pressure of 100 Pa for 20 seconds.
(2) A raw material gas not having been deposited is evacuated from the inside of the system through argon purging for 15 seconds.
(3) A reactive gas is introduced into the deposition reaction portion, and the precursor thin-film and the reactive gas are caused to react with each other at a system pressure of 100 Pa for 20 seconds.
(4) An unreacted reactive gas and a by-product gas are evacuated from the inside of the system through argon purging for 15 seconds.

Example 6

A thin-film was manufactured on the surface of a ruthenium wafer by the same method as in Example 5 except that Compound No. 19 was used as the thin-film forming raw material, the reaction temperature was changed to 300° C., and the number of the cycles was changed to 300. When the composition of the thin-film was analyzed by X-ray photoelectron spectroscopy, it was recognized that the thin-film was a thin-film containing cobalt, and the content of residual carbon was less than 0.1 atom %, which was a detection limit. In addition, when the film thickness of the thin-film was measured by scanning electron microscopy, the thin-film formed on the surface of the ruthenium wafer was a smooth and flat film having a film thickness of 6 nm, and the film thickness obtained per cycle was about 0.02 nm.

Example 7

A thin-film was manufactured on the surface of a copper wafer by the same method as in Example 6 except that the ruthenium wafer was changed to a copper wafer. When the composition of the thin-film was analyzed by X-ray photoelectron spectroscopy, it was recognized that the thin-film was a thin-film containing cobalt, and the content of residual carbon was less than 0.1 atom %, which was a detection limit. When the film thickness of the thin-film was measured by scanning electron microscopy, the thin-film formed on the surface of the copper wafer was a smooth and flat film having a film thickness of 3 nm, and the film thickness obtained per cycle was about 0.01 nm.

Comparative Example 6

A thin-film containing copper was manufactured on the surface of a ruthenium wafer by the same method as in Example 5 except that Compound No. 1 was changed to Comparative Compound 2, and the raw material container temperature was changed from 120° C. to 140° C. However, a smooth and flat film was not able to be formed. In addition, residual carbon was detected in the obtained film.

Comparative Example 7

A thin-film containing cobalt was manufactured on the surface of a ruthenium wafer by the same method as in Example 6 except that Compound No. 19 was changed to Comparative Compound 3, and the raw material container temperature was changed from 120° C. to 140° C. However, a smooth and flat film was not able to be formed. In addition, residual carbon was detected in the obtained film.

Comparative Example 8

A thin-film containing cobalt was manufactured on the surface of a copper wafer by the same method as in Comparative Example 7 except that the ruthenium wafer was changed to a copper wafer. However, a smooth and flat film was not able to be formed. In addition, residual carbon was detected in the obtained film.

From the result of Comparative Example 1, it was difficult to produce the compound in which, in the formula (1), R's except for $R^2$, $R^3$, and $R^4$ each represented a group containing a fluorine atom.

The reason why a satisfactory thin-film was not able to be manufactured in each of Comparative Examples 6, 7, and 8 is considered as follows: the raw material container temperature was required to be increased because each of Comparative Compounds 2 and 3 had a low vapor pressure, and thermal decomposition occurred in each of Comparative Compounds 2 and 3 under the condition of a raw material container temperature of 140° C.

It was able to be recognized from the foregoing that when, of the compounds represented by the formula (1), the compound in which at least one of $R^2$, $R^3$, and $R^4$ is substituted with a group containing a fluorine atom was used as the thin-film forming raw material, a high-quality thin-film having high volatility was able to be manufactured.

The invention claimed is:

1. A compound represented by the following formula (1):

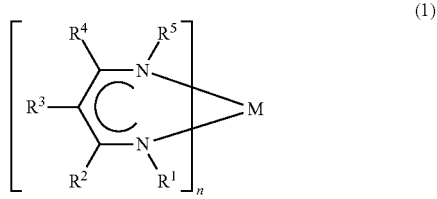

in the formula (1), $R^1$ to $R^5$ each independently represent a hydrogen atom, an alkyl group having 1 to 5 carbon atoms, or a group containing a fluorine atom, M represents a metal atom, and "n" represents a valence of the metal atom represented by M, provided that $R^1$ and $R^5$ each represent an alkyl group having 1 to 5 carbon atoms, at least one of $R^2$ and $R^4$ represents an alkyl group having 1 to 5 carbon atoms substituted with a fluorine atom, and $R^3$ represents a hydrogen atom.

2. The compound according to claim 1, wherein the group containing a fluorine atom is an alkyl group having 1 to 5 carbon atoms substituted with a fluorine atom.

3. The compound according to claim 1, wherein M in the formula (1) represents a metal atom selected from copper, nickel, cobalt, tin, manganese, and zinc.

4. A thin-film forming raw material, comprising the compound of claim 1.

5. A method of manufacturing a thin-film, comprising:
    introducing a raw material gas obtained by vaporizing the thin-film forming raw material of claim 4 into a treatment atmosphere having a substrate set therein; and
    subjecting the compound in the raw material gas to decomposition and/or a chemical reaction, to thereby form a metal-containing thin-film on a surface of the substrate.

\* \* \* \* \*